(12) United States Patent
Chitturi et al.

(10) Patent No.: US 7,348,556 B2
(45) Date of Patent: Mar. 25, 2008

(54) METHOD OF MEASURING THREE-DIMENSIONAL SURFACE ROUGHNESS OF A STRUCTURE

(75) Inventors: Prasanna Chitturi, Hillsboro, OR (US); Liang Hong, Hillsboro, OR (US); Craig Henry, Aloha, OR (US); John Notte, Gloucester, MA (US)

(73) Assignee: FEI Company, Hillsboro, OR (US)

( * ) Notice: Subject to any disclaimer, the term of this patent is extended or adjusted under 35 U.S.C. 154(b) by 316 days.

(21) Appl. No.: 11/252,115

(22) Filed: Oct. 17, 2005

(65) Prior Publication Data

US 2007/0018099 A1   Jan. 25, 2007

Related U.S. Application Data

(60) Provisional application No. 60/700,654, filed on Jul. 19, 2005.

(51) Int. Cl.
*H01J 37/30* (2006.01)
(52) U.S. Cl. .................. 250/309; 250/307; 250/310
(58) Field of Classification Search ............... 250/307, 250/310, 492.21
See application file for complete search history.

(56) References Cited

U.S. PATENT DOCUMENTS

| | | | |
|---|---|---|---|
| 5,435,850 A | 7/1995 | Raqsmussen | |
| 5,851,413 A | 12/1998 | Casella et al. | |
| 6,889,113 B2* | 5/2005 | Tasker et al. | 700/180 |
| 2001/0010356 A1* | 8/2001 | Talbot et al. | 250/307 |
| 2006/0226359 A1* | 10/2006 | Principe | 250/310 |

* cited by examiner

*Primary Examiner*—Jack I. Berman
*Assistant Examiner*—Michael J Logie
(74) *Attorney, Agent, or Firm*—Scheinberg & Griner, LLP; David Griner; Michael O. Scheinberg

(57) ABSTRACT

An improved method of measuring the three-dimensional surface roughness of a structure. A focused ion beam is used to mill a succession of cross-sections or "slices" of the feature of interest at pre-selected intervals over a pre-selected measurement distance. As each cross-section is exposed, a scanning electron microscope is used to measure the relevant dimensions of the feature. Data from these successive "slices" is then used to determine the three-dimensional surface roughness for the feature.

24 Claims, 12 Drawing Sheets

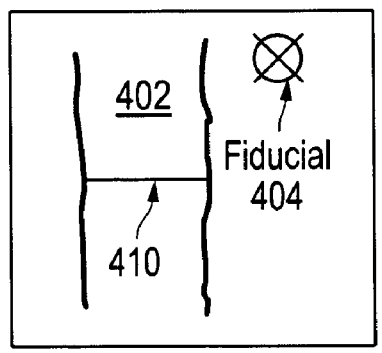 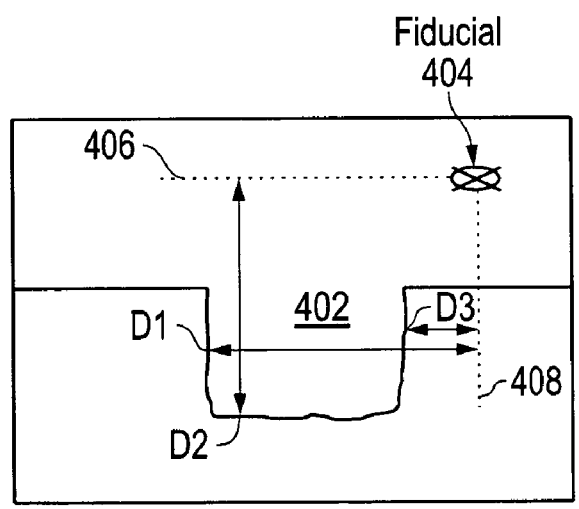
*FIG. 4A*                *FIG. 4B*

METHOD OF MEASURING THREE-DIMENSIONAL SURFACE ROUGHNESS OF A STRUCTURE

This application claims priority from U.S. Provisional Application No. 60/700,654, filed on Jul. 19, 2005.

TECHNICAL FIELD OF THE INVENTION

The present invention relates to charged particle beam processing and, in particular, to a method of determining three-dimensional surface roughness for a structure.

BACKGROUND AND SUMMARY OF THE INVENTION

Semiconductor manufacturing, such as the fabrication of integrated circuits, typically entails the use of photolithography. A semiconductor substrate on which circuits are being formed, usually a silicon wafer, is coated with a material, such as a photoresist, that changes solubility when exposed to radiation. A lithography tool, such as a mask or reticle, positioned between the radiation source and the semiconductor substrate casts a shadow to control which areas of the substrate are exposed to the radiation. After the exposure, the photoresist is removed from either the exposed or the unexposed areas, leaving a patterned layer of photoresist on the wafer that protects parts of the wafer during a subsequent etching or diffusion process.

The photolithography process allows multiple integrated circuit devices or electromechanical devices, often referred to as "chips," to be formed on each wafer. The wafer is then cut up into individual dies, each including a single integrated circuit device or electromechanical device. Ultimately, these dies are subjected to additional operations and packaged into individual integrated circuit chips or electromechanical devices.

During the manufacturing process, variations in exposure and focus require that the patterns developed by lithographic processes be continually monitored or measured to determine if the dimensions of the patterns are within acceptable ranges. The importance of such monitoring, often referred to as process control, increases considerably as pattern sizes become smaller, especially as minimum feature sizes approach the limits of resolution available by the lithographic process. In order to achieve ever-higher device density, smaller and smaller feature sizes are required. This may include the width and spacing of interconnecting lines, spacing and diameter of contact holes, and the surface geometry such as corners and edges of various features. Features on the wafer are three-dimensional structures and a complete characterization must describe not just a surface dimension, such as the top width of a line or trench, but a complete three-dimensional profile of the feature. Process engineers must be able to accurately measure the critical dimensions (CD) of such surface features to fine tune the fabrication process and assure a desired device geometry is obtained.

As a result, careful monitoring of surface roughness for features is becoming increasingly important. As design rules shrink, the margin for error in processing becomes smaller. Even small deviations from design dimensions may adversely affect the performance of a finished semiconductor device. Characteristics such as profile roughness, such as roughness along the bottom of trenches or on the sidewalls of lines, which could be ignored for larger features, now consumes a large amount of the tolerance budget.

In this application, the phrase profile roughness will include both roughness on one edge of a feature, referred to as line edge roughness (LER), and roughness of the entire feature, referred to as line width roughness (LWR). It should be recognized that the terms "line edge roughness" and "edge roughness" are often used to refer to roughness characteristics of structures other than just lines. For example, the roughness characteristic of a two-dimensional structure, such as a via or hole, is also often referred to as a line edge roughness or edge roughness. In this application, the following description, the terms "line edge roughness" and "edge roughness" are also used in this broad sense.

A number of different methods of measuring profile roughness are known in the prior art. Various optical methods, such as optical profilometry or scatterometry, can be used to rapidly determine surface roughness. However, the resolution of optical methods is limited, typically greater than 0.5 micron, and such methods do not directly measure surface topography.

Mechanical profilers, such as scanning probe microscopes, can be used to generate very detailed three-dimensional measurements of surface roughness. However, mechanical profilers are typically very slow. Resolution is limited by the size of the probe or stylus, and very small probes are difficult to manufacture and are very fragile. Also, measurement of features with high-aspect ratios or undercut surfaces is very difficult using any type of stylus profilometer.

Some types of profile roughness, such as LER and LWR, can be monitored using electron beam techniques. The scanning electron microscope (SEM) allows for the production of an image of greater magnification and higher resolution than can be achieved by the best optical microscopes. An SEM produces a finely focused beam of electrons, which is scanned across the surface of a work piece, typically in a raster pattern. The electrons that make up the electron beam are called primary electrons. When the electron beam is directed at the work piece surface, the primary electrons collide with electrons in orbit around the nuclei of the atoms present in the work piece causing the emission of secondary electrons. Some of the primary electrons will also be reflected from the work piece surface. These higher energy electrons (>50 eV) are called backscattered electrons. Both types of electrons can be detected by inserting an appropriate detector near the specimen. The detector produces a variable voltage output; the more secondary or backscattered electrons it detects, the greater will be the voltage generated.

Typically, to measure the width of a structure, the SEM is used in conjunction with automatic metrology software. As the electron beam is scanned across the exposed cross-section, whether secondary or backscattered detection is employed, there will typically be a change in electron intensity at the edges of the structure. This change can be due to a change to topography or to a transition between two different materials. An algorithm is used to assign an edge position based upon the contrast at the edges of the structure and to determine the distance between those edges.

The SEM alone, however, can only view a feature from the top down. While overall roughness can be measured, it is very difficult to determine whether the roughness is at the bottom or top of the feature. Further, the SEM, like the optical and mechanical methods discussed above, can only be used to measure surface features. The profile roughness of buried features or features surrounded by other materials cannot be measured using these methods.

It is possible to get more accurate information of a feature profile and to measure buried features by using a charged particle beam system, such as a focused ion beam system (FIB), in conjunction with a scanning electron microscope (SEM). FIB systems are widely used in microscopic-scale manufacturing operations because of their ability to image, etch, mill, deposit, and analyze very small structures with great precision. FIB systems produce a narrow, focused beam of charged particles (hereinafter referred to as ions) that is typically scanned across the surface of a work piece in a raster fashion, similar to a cathode ray tube. In most commercial FIB systems, the ions used are positively charged gallium ions ($Ga^+$) extracted from liquid metal ion sources. The extracted ions are accelerated collimated, and focused onto a work piece by a series of apertures and electrostatic lenses. The ion beam can be used to remove material from the work piece surface or to deposit material onto the surface. When used to remove material, often referred to as milling, the heavy gallium ions in the focused ion beam physically eject atoms or molecules from the surface by sputtering, that is, by a transfer of momentum from the incoming ions to the atoms at the surface.

The FIB system can be used to expose the cross-section of a feature, so that the profile of the feature can be accurately measured. Once the cross-section is exposed, a scanning electron microscope can be used to measure the profile of the feature. This measurement, however, is still only a two dimensional measurement at one particular point. Three-dimensional measurement is required to understand the presence of dimensional variations such as standing waves or changes in slope and to adequately control all of the factors that contribute to increase in roughness, such as pattern transfer, deposition, or planarization.

Thus, there is still a need for an improved method of measuring the three-dimensional surface roughness of a semiconductor feature.

SUMMARY OF THE INVENTION

It is an object of the invention, therefore, to provide an improved method of measuring the three-dimensional surface roughness of a structure.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which:

FIG. 4A shows a top-down FIB image of a trench with a fiducial milled at a location within the field of view but separated from the feature of interest.

FIG. 4B shows an SEM image of a cross section of the trench of FIG. 8A.

DETAILED DESCRIPTION OF PREFERRED EMBODIMENTS

Preferred embodiments of the present invention are directed to methods and an apparatus for measuring the three-dimensional surface roughness of a structure or feature. In a preferred embodiment of the present invention, the sample to be measured is loaded into a dual beam FIB-SEM. The FIB is used to mill a succession of cross-sections or "slices" of the feature of interest at pre-selected intervals over a pre-selected measurement distance. As each cross-section is exposed, the SEM is used to measure the relevant dimensions of the feature. Data from these successive "slices" is then used to determine the three-dimensional surface roughness for the feature.

Although much of the following description is directed toward the measurement of the width of a structure, the methods of the present invention are equally applicable to any relevant dimension, including height, slope, sidewall angle, etc. Further, although much of the following description is also directed toward the use of focused ion beams to mill the cross-section and electron beams to image and measure the cross-section, the methods of the present invention could equally be utilized with other milling and imaging techniques including other types of charged particle beam systems, electron beam milling, or optical processing. Hence, the scope of the present invention should not be limited to the specific embodiments discussed herein.

Figure 1A:
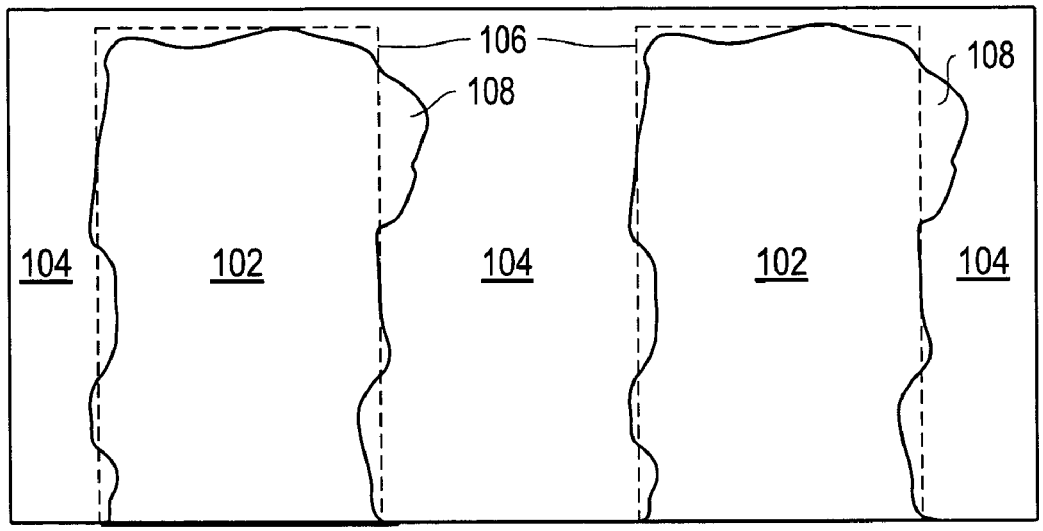
FIG. 1A and FIG. 1B are schematic representation of cross-sections of lines 101 and 102 showing edge roughness on the sidewalls and tops of each line.
Figure 1B:
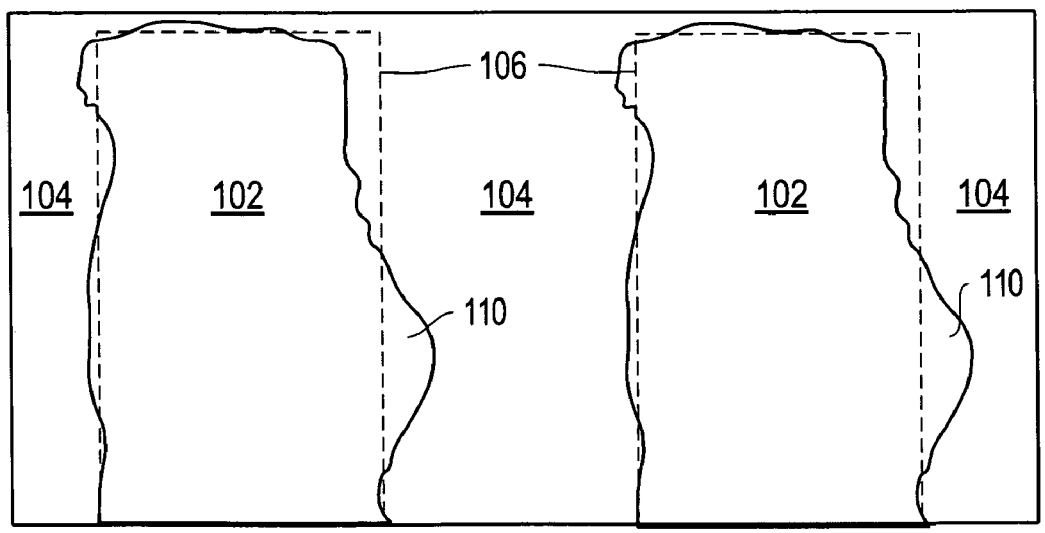

FIG. 1A and FIG. 1B are schematic representation of cross-sections of lines 101 and 102 showing edge roughness on the sidewalls and tops of each line. Lines 101 and 102 are surrounded by insulating material 105. Dashed lines 106 illustrate the ideal cross-section for each line. In FIG. 1A, lines 101 show a pronounced roughness 108 toward the top of the right sidewall. In FIG. 1B, lines 102 show a pronounced roughness 110 toward the bottom of the right sidewall. If lines 102 and 103 were viewed from the top down, as when using a prior art CD-SEM to determine line edge roughness, lines 101 and lines 102 would look very similar. An accurate understanding of the exact three-dimensional variation in the line edge can assist in determining and correcting the source of the variation.

Figure 1C:
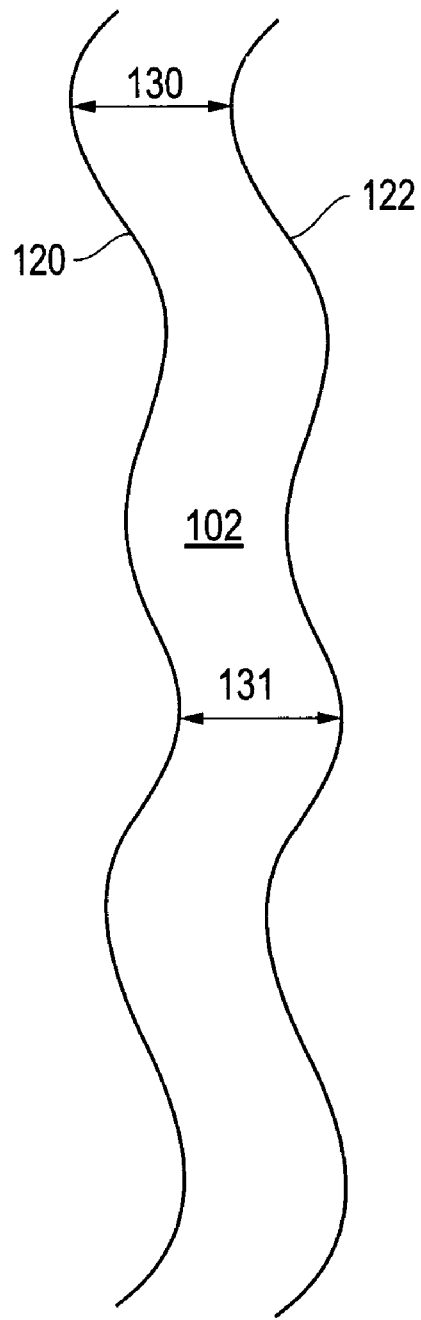
FIGS. 1C and 1D are schematic diagrams of line edges illustrating two different types of line edge roughness.
Figure 1D:
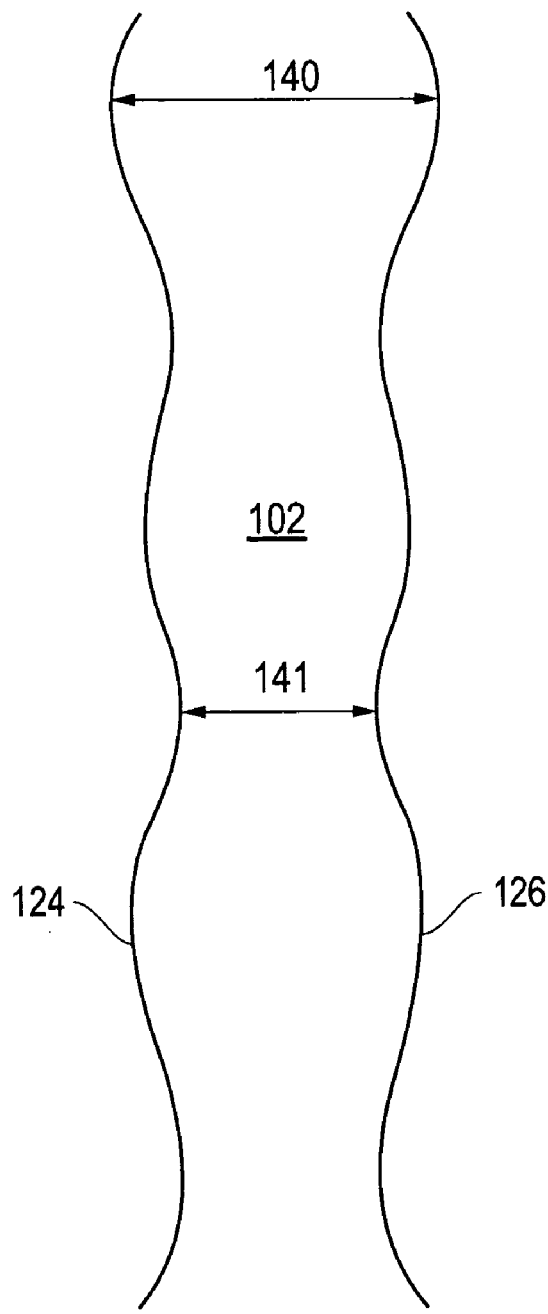

FIGS. 1C and 1D are schematic diagrams of line edges illustrating two different types of line edge roughness. FIG. 1C illustrates line edge roughness where roughness on the left edge 120 of line 103 correlates with roughness on the right edge 122. In other words, the width of the line 102 is constant but the line itself is wavy. As a result, the overall CD (width of the line) at point 130 is the same as the CD at point 131. FIG. 1D illustrates line edge roughness case where the right edge 126 and left edge 124 of the line 104 are synchronous but fluctuate in the opposite directions from FIG. 1C. Thus, in FIG. 1D, the line CD at 140 will be greatly different from the CD at 141. Other types of line edge roughness exist, for example the right and left edges may fluctuate independently so that there is no correlation.

Figure 2:
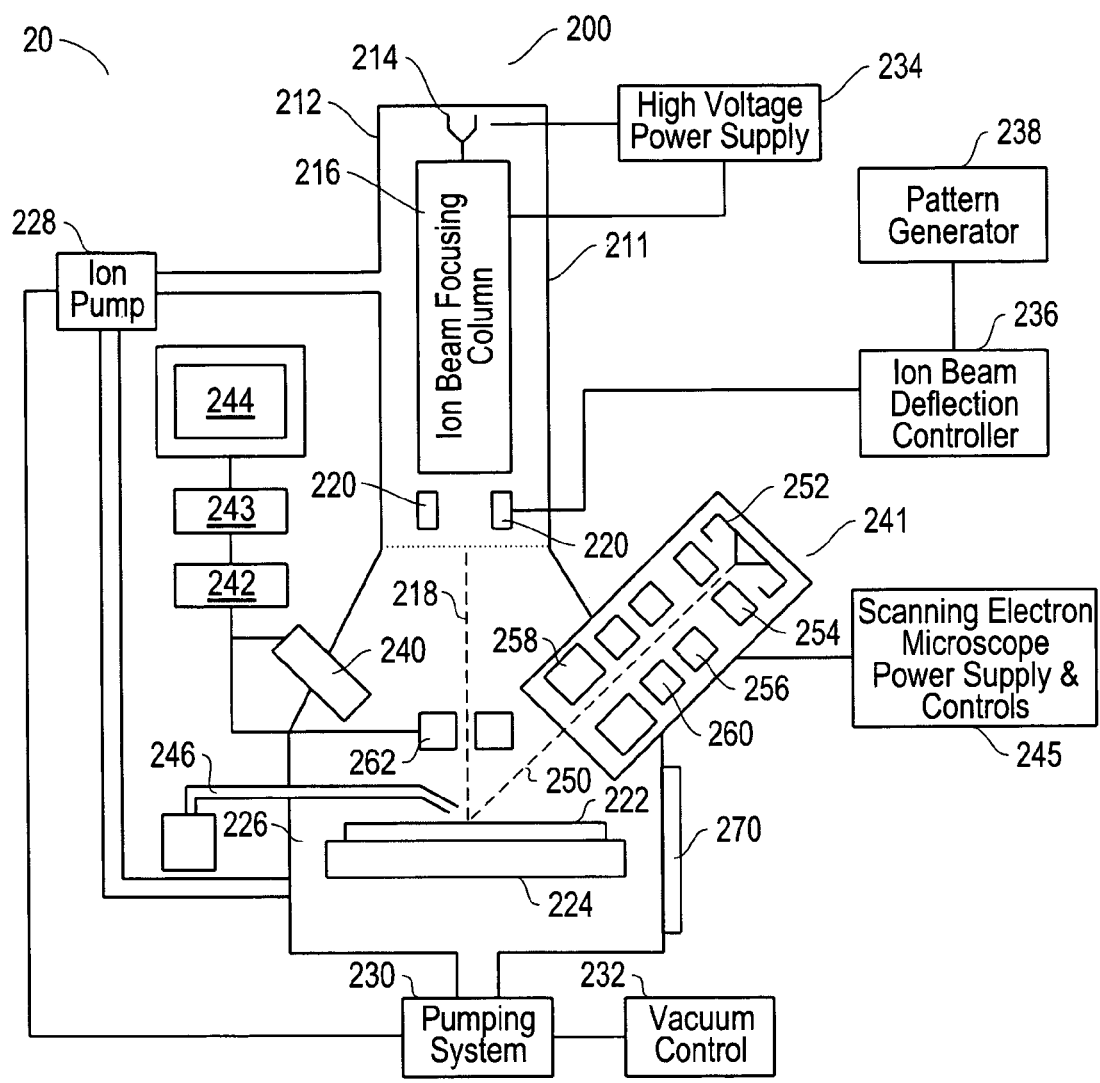
FIG. 2 shows a typical dual beam FIB/SEM system 20 used to implement one aspect of the present invention.

FIG. 2 shows a typical dual beam FIB/SEM system 20 used to implement one aspect of the present invention. With reference to FIG. 2, one embodiment of the present invention utilizes a dual beam FIB/SEM system 20 that uses an ion beam that is either normal or tilted by a few degrees to the plane of the workpiece surface and an electron beam having an axis that is also tilted, e.g., 52 degrees from the axis of ion beam. In some embodiments, the ion beam and electron beam are capable of aligning so that the fields of view of both beams are coincident to within a few microns or less. The ion beam is typically used to image and machine the work piece, and the electron beam is used primarily for imaging but can also be used for some modification of the work piece. The electron beam will typically produce an image of a higher resolution than the ion beam image, and it will not damage the viewed surface like the ion beam. The image formed by the two beams can look different, and the two beams can therefore provide more information than a single beam. Such a dual beam system could be made from discrete components or alternatively, could be derived from a conventional device such as an Altura™ or an Expida™ system available from FEI Company of Hillsboro, Oreg.

Focused ion beam system 200 includes an evacuated envelope 211 having an upper neck portion 212 within which are located an ion source 214 and a focusing column 216 including extractor electrodes and an electrostatic optical system. Ion beam 218 passes from ion source 214 through column 216 and between electrostatic deflection means schematically indicated at 220 toward sample 222, which comprises, for example, a semiconductor device positioned on movable X-Y stage 224 within lower chamber 226. An ion pump 228 is employed for evacuating neck portion 212. The chamber 226 is evacuated with turbomolecular and mechanical pumping system 230 under the control of vacuum controller 232. The vacuum system provides within chamber 226 a vacuum of between approximately $1 \times 10^{-7}$ Torr and $5 \times 10^{-4}$ Torr. If an etch assisting, an etch retarding gas, or a deposition precursor gas is used, the chamber background pressure may rise, typically to about $1 \times 10^{-5}$ Torr.

High voltage power supply 234 is connected to ion source 214 as well as to appropriate electrodes in focusing column 216 for forming an ion beam 218 and directing the same downwardly. Deflection controller and amplifier 236, operated in accordance with a prescribed pattern provided by pattern generator 238, is coupled to deflection plates 220 whereby beam 218 may be controlled to trace out a corresponding pattern on the upper surface of sample 222. In some systems the deflection plates are placed before the final lens, as is well known in the art.

The ion source 214 typically provides a metal ion beam of gallium, although other ion sources, such as a multicusp or other plasma ion source, can be used. The ion source 214 typically is capable of being focused into a sub one-tenth micron wide beam at sample 222 for either modifying the sample 222 by ion milling, enhanced etch, material deposition, or for the purpose of imaging the sample 222. A charged particle multiplier 240 used for detecting secondary ion or electron emission for imaging is connected to amplifier 242. The amplified signals are converted into digital signals and subjected to signal processing by the signal processor unit 243. The resulting digital signal is to display an image of workpiece 222 on the monitor 244.

A scanning electron microscope 241, along with power supply and control unit 245, is also provided with the FIB system 200. An electron beam 250 is emitted from a cathode 252 by applying voltage between cathode 252 and an anode 254. Electron beam 250 is focused to a fine spot by means of a condensing lens 256 and an objective lens 258. Electron beam 250 is scanned two-dimensionally on the specimen by means of a deflection coil 260. Operation of condensing lens 256, objective lens 258, and deflection coil 260 is controlled by power supply and control unit 245.

Electron beam 250 can be focused onto workpiece 222, which is on movable X-Y stage 224 within lower chamber 226. Scanning electron microscope 241 produces a finely focused electron beam 250, which is scanned across the surface of the structure, preferably in a raster pattern. When the electrons in the electron beam 250 strike the surface of work piece 222, secondary electrons and backscattered electrons are emitted. Respectively, these electrons are detected by secondary electron detector 240 or backscattered electron detector 262. The analog signal produced either by secondary electron detector 240 or backscattered electron detector 262 is amplified by amplifier 242 and converted into a digital brightness value by signal processor unit 243. The resulting digital signal can be displayed as an image of workpiece 222 on the monitor 244.

As the electron beam 250 is scanned across the exposed cross-section, there will be a change in emitted electron intensity at the edges of the structure. An algorithm is used to assign an edge position based upon the difference in brightness values or contrast at either of the edges of the structure and to determine the distance between those edges. A typical system might use an electron beam current of 30 to 300 pA, a beam energy of 1 keV, and an electron beam current density of 2000 A/cm$^2$. A typical system might also use an electron beam spot size of 2 to 5 nm, a refresh period of approximately 0.5 to 5 seconds, and a scanning field width of 0.5 to 5.0 microns. Again, skilled persons can readily determine appropriate beam characteristics to suit a particular application.

A gas delivery system 246 extends into lower chamber 226 for introducing and directing a gaseous vapor toward sample 22. U.S. Pat. No. 5,851,413 to Casella et al. for "Gas Delivery Systems For Particle Beam Processing," assigned to the assignee of the present invention, describes a suitable fluid delivery system 246. Another gas delivery system is described in U.S. Pat. No. 5,435,850 to Rasmussen for a "Gas Injection System," also assigned to the assignee of the present invention.

A door 270 is opened for inserting sample 222 onto stage 224, which may be heated or cooled, and also for servicing an internal gas supply reservoir, if one is used. The door is interlocked so that it cannot be opened if the system is under vacuum. The high voltage power supply provides an appropriate acceleration voltage to electrodes in ion beam column 216 for energizing and focusing ion beam 218. Dual beam FIB/SEM systems are commercially available, for example, from FEI Company, Hillsboro, Oreg., the assignee of the present application.

Figure 3:
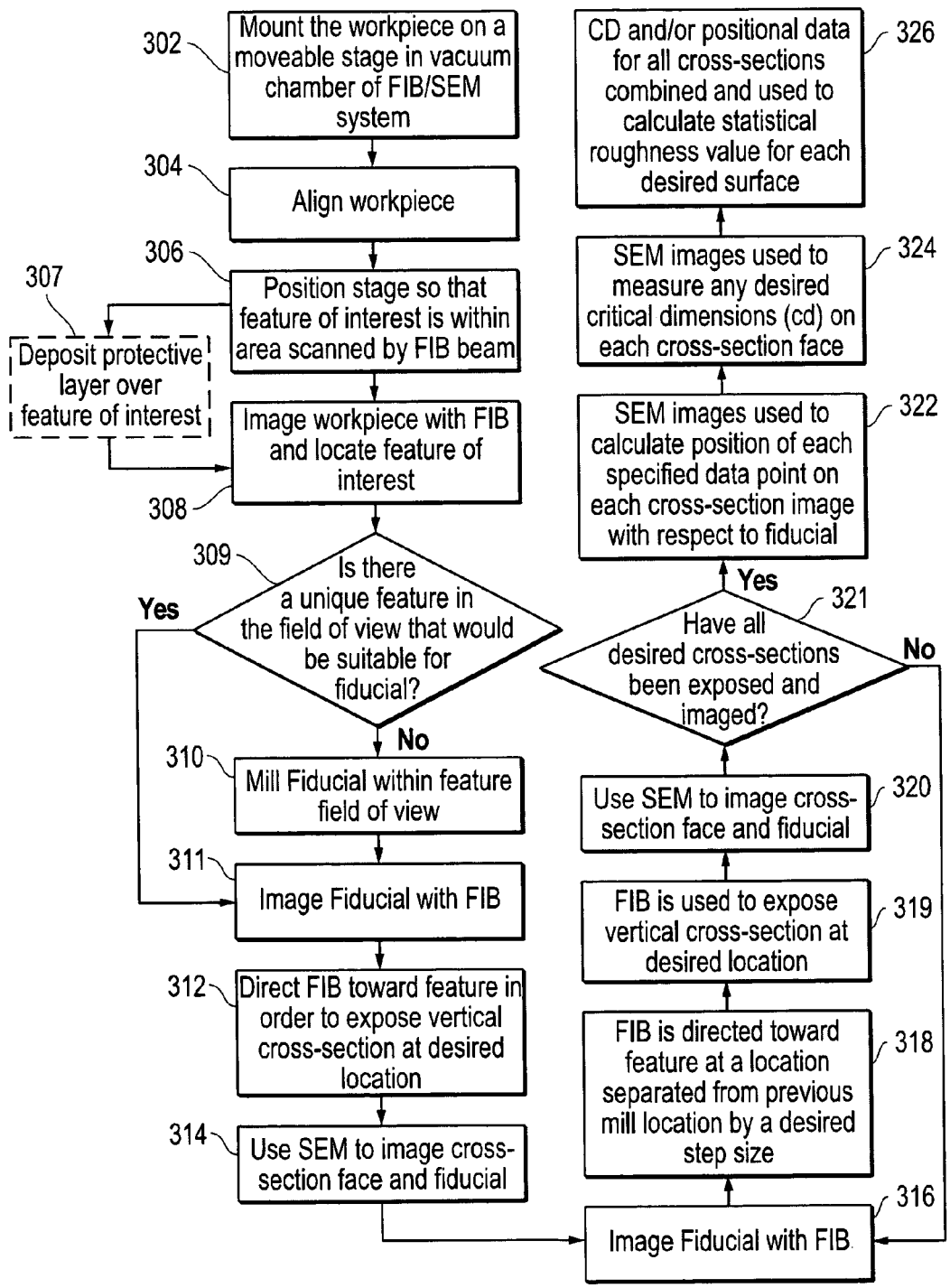
FIG. 3 is a flowchart showing the steps of measuring three-dimensional surface roughness according to a preferred embodiment of the present invention.

FIG. 3 is a flowchart showing the steps of measuring three-dimensional surface roughness according to a preferred embodiment of the present invention.

In step 302, the workpiece is loaded into an FIB/SEM system such as the one illustrated in FIG. 2 by mounting the workpiece on the FIB/SEM stage. The workpiece can be loaded manually or automatically, for example by an automatic handler system.

In step 304, the workpiece is aligned. This alignment can also be accomplished manually, for example by an operator using an optical microscope, or automatically, for example by using an automatic handler robot which locates a notch or flat edge of the workpiece in order to determine the proper orientation.

In step 306, the stage is positioned so that the feature of interest is within the target area scanned by the charged particle beam (the field of view). This positioning can be accomplished, for example, by storing and using positional coordinates.

In optional step 307, a protective layer can be deposited on the workpiece in order to protect the feature of interest during the milling process. Because FIB sputter milling can cause significant damage to small structures, the structure surface is often coated with a protective layer of material such as tungsten before milling begins. Such a layer can be deposited using a gas that decomposes in the presence of the ion beam and deposits material onto the surface. This process is commonly referred to as FIB-induced chemical vapor deposition (CVD). Typically the precursor gas, such as tungsten hexacarbonyl gas, is directed onto the work piece surface, usually via a fine needle inserted near the position of the ion beam. The gas is broken down into volatile and non-volatile components by the low energy electrons generated when the ion beam strikes the surface. The non-volatile component, in this case the protective tungsten coating, is deposited onto the surface, while the volatile component is pumped away.

In step 308, the workpiece is imaged with the FIB to locate the feature of interest. In step 309, the FIB imaging is used to determine whether there is a unique feature within the field of view that is suitable to serve as a fiducial or reference point for the ion beam. Factors such as system drift make the positioning of the ion beam somewhat variable at the nanometer scale. The fiducial allows an independent reference to determine the precise x-y coordinates of each milled cross-section. An appropriate fiducial should be a unique feature within the field of view that can be consistently identified. A preferred fiducial will also allow the beam location to be pinpointed in both the x and y directions. For example, one suitable fiducial might be the intersection of two lines (a cross-shaped fiducial). The point of intersection can be easily identified by the FIB imaging and the positional data used as a reference point for subsequent positioning of each cross-section. Preferably, an appropriate fiducial will have an axis which is parallel to each feature surface for which roughness is to be determined.

If an appropriate structure is not present on the surface of the workpiece, in step 310 a fiducial mark can be milled at a location within the field of view but separated from the feature of interest, preferably in a location that will not be damaged when the feature is cross-sectioned. If a fiducial is milled into the surface, it is preferably created after any protective layer has been deposited. A fiducial may be milled using any suitable method, including for example, focused ion beam sputtering, gas-assisted etching, or electron beam induced gas-assisted etching. The fiducial can be made of a shape that is readily distinguishable so that it can be consistently identified and located. The fiducial is preferably not rotationally symmetric so that the orientation of the fiducial can be determined upon subsequent inspection. FIG. 4A, discussed in greater detail below, shows a milled fiducial 404 next to the feature of interest, in this case trench 402.

In step 311, the fiducial is imaged by the ion beam. During FIB imaging of the fiducial, a partial scan may be used to prevent damaging the feature of interest under the FIB. The fiducial's positional data is then used as a reference point for subsequent positioning of the ion beam at each desired cross-section location.

In step 312, the ion beam is directed to the feature of interest at a known location relative to the fiducial and used to expose a cross-section of the feature by milling through any protective layer and the feature itself. Typically, the feature of interest will have a known structure so that the required milling depth can be easily determined. In order to expose a cross-section, the ion beam will preferably be scanned within a virtual mill box having a width, which is parallel to the desired cross section face, and a height, which is perpendicular to the desired cross-section face. The use of virtual mill boxes to define a rectangular area on a target surface in which an ion beam will be directed is well known in the art. Preferably, the mill box width will be greater than the width of the feature to be measured. More preferably, the mill box width will be 1.5 times the milling depth. For the initial cross-section the height of the mill box will preferably be approximately 1.5 times the milling depth. This will allow a beam from a tilted SEM column to scan the cross-section face (alternately the sample could be tilted so that a vertical SEM column could be used).

The cross-section may be cut, for example, along the x-axis, the y-axis, or at a prescribed angle. For a feature such as conductive line, cross-sections will typically be transverse (perpendicular to the longitudinal axis of the feature). Preferably, the cross-section plane will be perpendicular to the surface being characterized.

Once the cross-section is exposed, in step 314, a scanning electron microscope is used to image the fiducial and the exposed cross-section face. Both the fiducial and the exposed cross-section face are preferably within the field of view of the SEM. The SEM images can be stored in any desired format (e.g., JPEG).

From the SEM image, the edge position and dimensions of the feature can be determined from the SEM image of the cross-section through the use of an algorithm that determines the location of two edges of the structure of interest. For example, to determine the width of a feature, the algorithm is used to assign an edge position based upon the contrast at the edges of the structure and to determine the distance between those edges.

In a similar fashion, the location of at least one axis of the fiducial is determined. An axis can be located, for example, by determining the edge positions for at least two substantially parallel fiducial surfaces (such as the opposite walls of a trench) and defining a line or axis halfway between the two edges. In some embodiments, an appropriate fiducial will have at least two fiducial axes, each substantially parallel to a feature surface for which roughness is to be determined.

In step 316, the fiducial is again imaged by the ion beam in order to ensure that the beam is properly aligned and that the location of the next cross-section can be accurately determined. In step 318, the ion beam is again directed to the feature of interest with the ion beam moved slightly from the previous mill (typically in a longitudinal direction). In step 319, the FIB is used to expose a cross-section at the new location. The mill box used to expose subsequent cross-sections (after the initial cross-section) can be smaller than the initial mill box. Although the width will typically remain the same, the height of the mill box can be less than 1.5 times the mill depth. The height of the mill box will be determined by the desired distance between successive cross-sections. Once a new cross-section is exposed, in step 320, a scanning electron microscope is again used to image the cross-section and the fiducial. Steps 316 through 320 are repeated until all desired cross-sections have been milled and imaged with the SEM.

In this fashion, a sequence of SEM images is obtained as the feature is progressively "sliced." Skilled persons will recognize that selecting the distance between each "slice" will involve a balancing of the precision needed for the roughness determination and the time required to complete the milling and imaging process. More precision is achieved if the scans are closer together, but the smaller the step size between slices, the more time will be required to complete the sample processing. For more accurate results, a step size that is less than the smallest expected roughness frequency should be selected. Typically, the step size for each successive slice will be less than 20 nm, preferably around 10 nm. Skilled persons will recognize that for process development, more accurate characterization of roughness is needed. As a result, for process development applications, small step sizes will be more appropriate. For process monitoring, however, it may be that few slices over a larger area will be sufficient. A feature will typically be sampled over a length of 1 μm to 2 μm, although larger or smaller distances can be used.

Once the slicing and imaging have been completed for the desired length of the feature, in step 322 the SEM images are used to calculate the position of each specified data point on each cross-section image by measuring the distance between each data point and the appropriate axis of the fiducial.

In step 324, the SEM images are used to measure any desired critical dimensions (CD) on each cross-section face. And finally, in step 326, the CD and/or positional data for all cross-sections is combined and used to calculate statistical roughness value for each desired surface. In order to more rapidly determine whether roughness is within acceptable margins, the data can be used to generate any of a number of known roughness parameters in order to characterize the feature surface, including root-mean-square roughness, peak-to-valley height, peak-to-peak roughness, spatial frequencies as determined by Fourier methods, or roughness orientation. The dimensions of each image can also be combined to determine three-dimensional information not available from a single image, such as volume, maximum width, maximum depth, taper angle, etc. The quantified characteristics may then be employed to refine the associated lithography processes to mitigate undesirable LER and/or linewidth variations. A complete three-dimensional profile of the surface texture of the feature can also be generated, often referred to as area roughness.

Skilled persons will recognize that some of the process steps shown in FIG. 3 can be carried out simultaneously as well as sequentially. For example, SEM images can be used to compute dimensions and roughness as each image is captured rather than after all of the cross-sections have been milled and imaged.

The overall throughput for the method of measuring three-dimensional surface roughness according to the present invention would typically be 5 to 7 minutes to expose and measure the first cross-section, and then 1 to 1.5 minutes for each slice thereafter. Depending upon the volume of data collected, such as the number of slices and the number of data points per cross-section, additional time may be required to process the data and calculate the desired roughness parameters.

FIGS. 4A and 4B illustrate how data points are measured relative to a fiducial according to the present invention. FIG. 4A shows a top-down FIB image of a trench 402 with a fiducial 404 milled at a location within the field of view but separated from the feature of interest. FIG. 4B shows an SEM image of a cross-section of trench 402 milled along line 410. The SEM image in 4B can be analyzed using automatic metrology software, as is well known in the art. An algorithm is used to assign an edge position based upon the contrast at the edges of the trench (the change in electron intensity). Likewise, the position of the fiducial is also determined, preferably by determining the edge positions and using those positions to define a fiducial axis halfway in between the edges. Once these determinations are made, values can be collected for the distance between data points D1, D2, and D3 and the fiducial axes 406 and 408.

Although only three data points are illustrated in FIG. 4B, any desired number of data points could be measured. Skilled persons will recognize that the number of data points required will depend upon a number of factors, such as whether the data is being used for process development or process monitoring. During process development, a larger number of data points would preferably be used so that the feature can be more accurately profiled. Typically, during process development, a number of samples of the particular feature of interest would be manufactured using slightly different parameters. Analysis of the surface roughness or possibly a three-dimensional characterization for each of these samples allows the manufacturing process to be optimized.

Figure 5A:
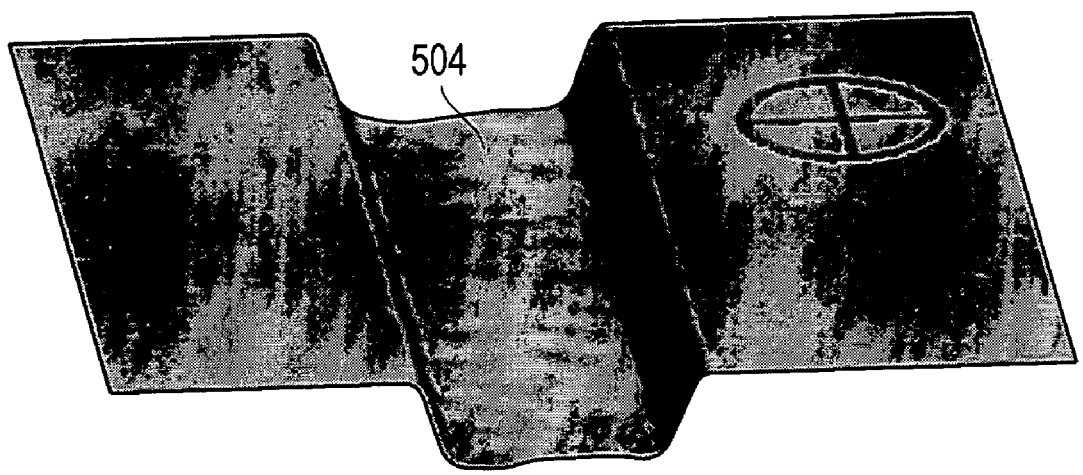
FIG. 5A shows a trench bottom with a non-oriented roughness with a large spatial frequency.
Figure 6A:
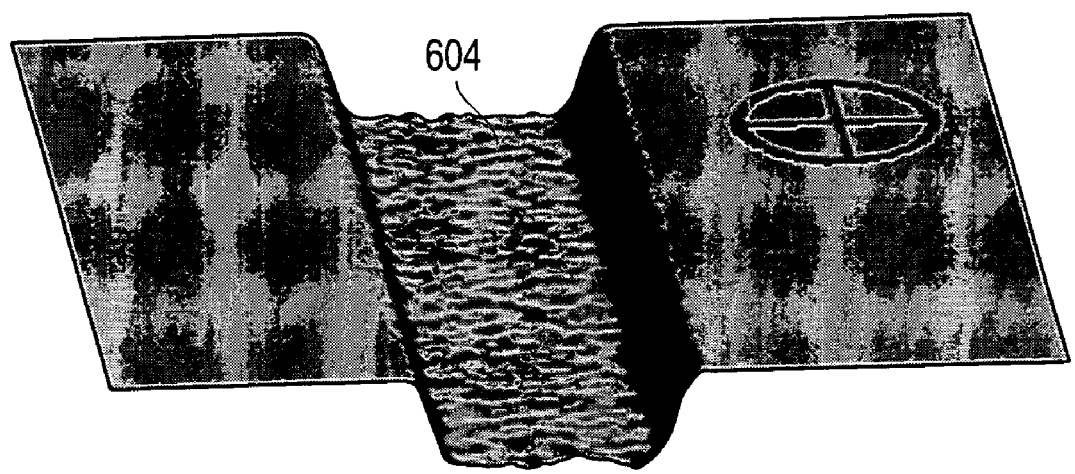
FIG. 6A shows a trench bottom with a non-oriented roughness with a small spatial frequency.
Figure 6B:
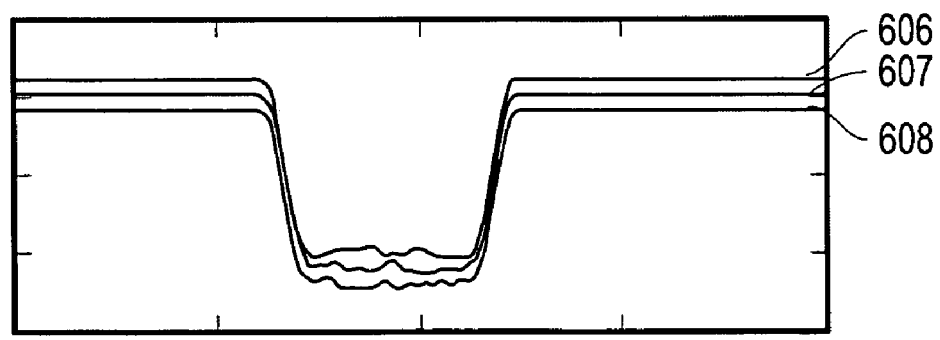
FIG. 6B shows three overlapping cross-sectional profiles of the trench shown in 5A.
Figure 7A:
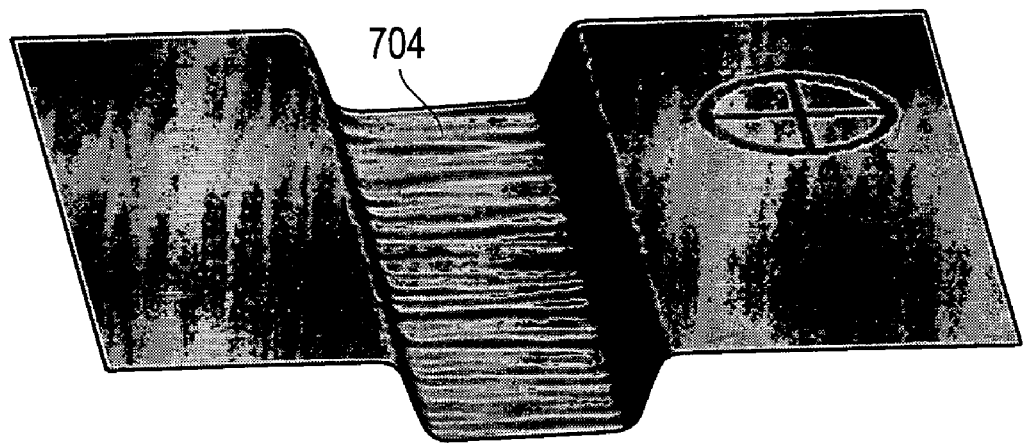
FIG. 7A shows a trench bottom with a horizontally oriented roughness.
Figure 7B:
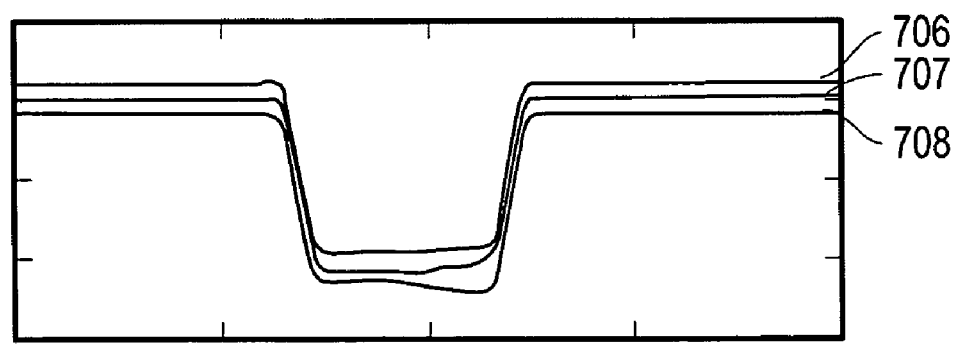
FIG. 7B shows three overlapping cross-sectional profiles of the trench shown in 6A.
Figure 8A:
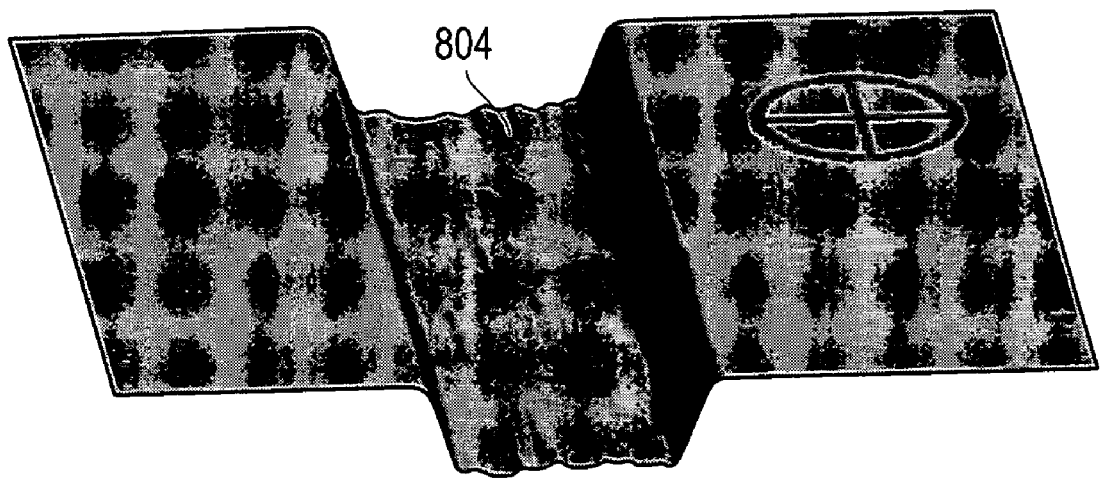
FIG. 8A shows a trench bottom with a vertically oriented roughness.
Figure 8B:
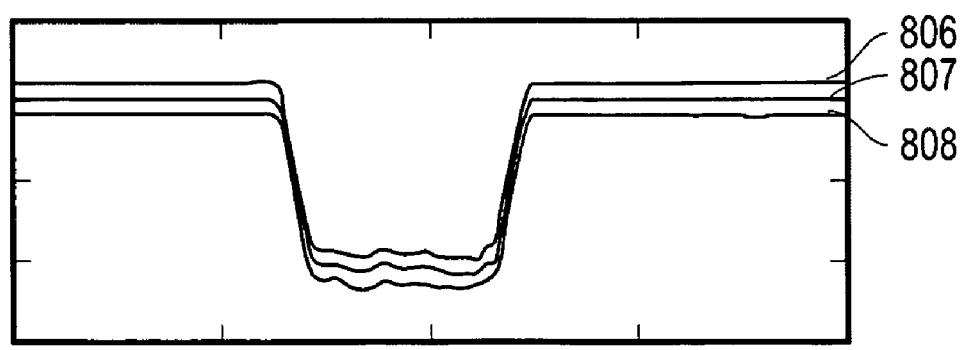
FIG. 8B shows three overlapping cross-sectional profiles of the trench shown in 7A.

For example, four different samples are shown in FIGS. 5A to 8A. Each example has a different type or degree of surface roughness on the bottom of a trench. FIG. 5A shows a trench bottom 504 with a non-oriented roughness with a large spatial frequency. FIG. 6A shows a trench bottom 604 with a non-oriented roughness with a small spatial frequency. FIG. 7A shows a trench bottom 704 with a horizontally oriented roughness. And FIG. 8A shows a trench bottom 804 with a vertically oriented roughness. Determining the three-dimensional surface roughness of the trench bottoms in these four samples could help optimize the manufacturing process. In this very simple example, FIG. 5A shows the least surface roughness along the trench bottom. As a result the manufacturing process should follow the parameters used to manufacture the trench shown in 5A.

Process monitoring, however, might require many fewer data points to sufficiently characterize surface roughness for a feature. At the process monitoring stage, the parameters which are sensitive to process variations and the dimensional deviations which can result will have been identified in process development. Thus, process monitoring using the present invention will typically require fewer cross-sections and a relatively low number of data points for each cross-section. The exact number required will depend upon what kind of dimensional deviation can be expected for a given manufacturing process.

Figure 5B:
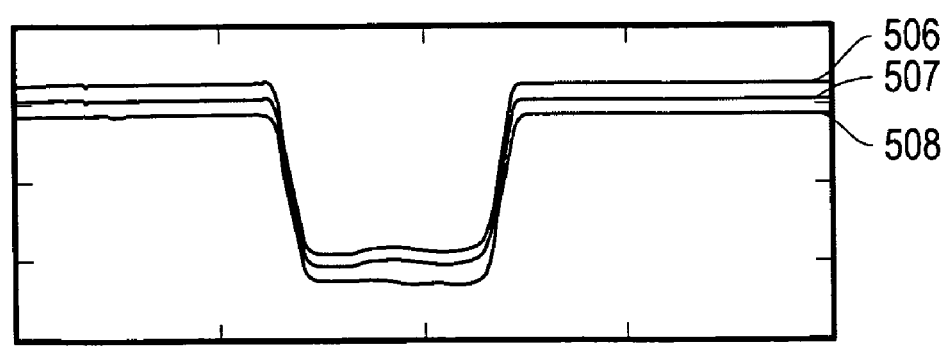
FIG. 5B shows three overlapping cross-sectional profiles of the trench shown in 4A.

For example, FIGS. 5B though 8B show three cross-sectional profiles of the trench shown in corresponding FIGS. 5A through 8A. If the cross-sectional profiles shown in FIG. 5B (506, 507, & 508) represent the desired or optimal structure, and if the types of expected process variations could produce a trench with the cross-sectional profiles shown in FIG. 6B (606, 607, & 608), one data point on the trench floor would probably not be sufficient to determine whether a given sample has a trench floor roughness like FIG. 5A or like FIG. 6A.

As shown in the cross-sectional profiles of FIG. 6B, the bottom of the trench shown in FIG. 6A has a degree of variation in the surface of the trench bottom across each cross section. There is also a degree of variation between each cross-section. In this instance, it might be sufficient to measure two or three data points along the trench bottom for each cross section. This should be sufficient to detect any significant increase in the degree of variation (as when the samples started looking less like FIG. 5A and more like FIG. 6A).

The same would be true where the expected process deviations could produce a trench bottom like the one illustrated in FIG. 8A. As seen in the cross-section profiles in FIG. 8B (806, 807, & 808), the bottom of the trench shown in FIG. 8A has a more significant degree of variation in the surface of the trench bottom across each cross section. However, there is very little variation between each cross-section. As a result, the development of the kind and degree of roughness shown in FIGS. 8A and 8B might require more data points along the bottom of each cross section, but might require fewer slices (more distance between cross-sections).

A different situation is shown in FIGS. 7A and 7B. FIG. 7A shows a trench bottom with a horizontally oriented roughness. If the trench shown in FIG. 7A is cross-sectioned and measured according to the present invention, only one data point may be sufficient to monitor for an increase in this type of roughness. As seen in cross-sectional profiles 706, 707, & 708 in FIG. 7B, because the roughness is oriented generally parallel to the cross-section face, multiple data points along the trench bottom will have generally the same values, while the data points on different cross-sections will be drastically different depending upon the location of the cross-section relative to the roughness frequency.

Figure 9A:
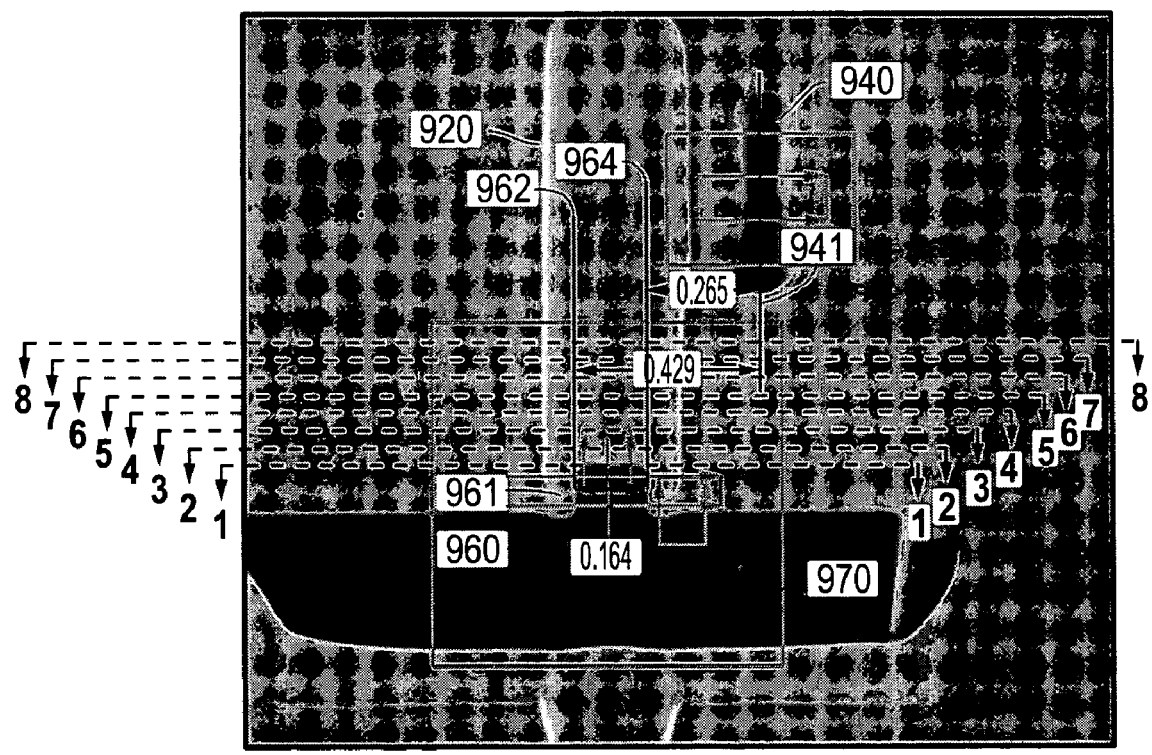
FIG. 9A is an SEM image of a conductive line that has been cross-sectioned and measured at several data points according to one embodiment of the present invention.

FIG. 9A is an SEM image of a line that has been cross-sectioned and measured according to one embodiment of the present invention. In FIG. 9A, the feature of interest 920 comprises a conductive line 960 that has been covered with a protective layer to protect line 960 during FIB milling. Fiducial 940, in this case a simple trench, has been milled with the field of view. In many instances, a preferred fiducial would provide a reference in both the x and y directions. In this simplified example, however, the measurements are only in one axis so a fiducial with only one identifiable axis can be used. In FIG. 9A, the feature cross-section has been exposed along cross-section line 1. Cross section lines 2 through 8 show the locations of subsequent cross-sections that will be exposed and measured.

Typically, the FIB milling is accomplished by way of a user-defined virtual "mill box" (not shown) that determines where the FIB is directed. According to the present invention, when the first cross-section in the sequence is exposed, the height of the mill box (along the y axis) will preferably be greater than the required mill depth. This allows a tilted SEM to image the entire cross-section face and the fiducial. (Although the image will be skewed if the electron beam is oriented at an angle to the cross-section face, the image can be corrected through the use of well-known software.) For subsequent cross-sections cs2 through cs8, the height of the mill box will be equal to the desired slice step size (the distance between cross-sections).

Figure 9B:
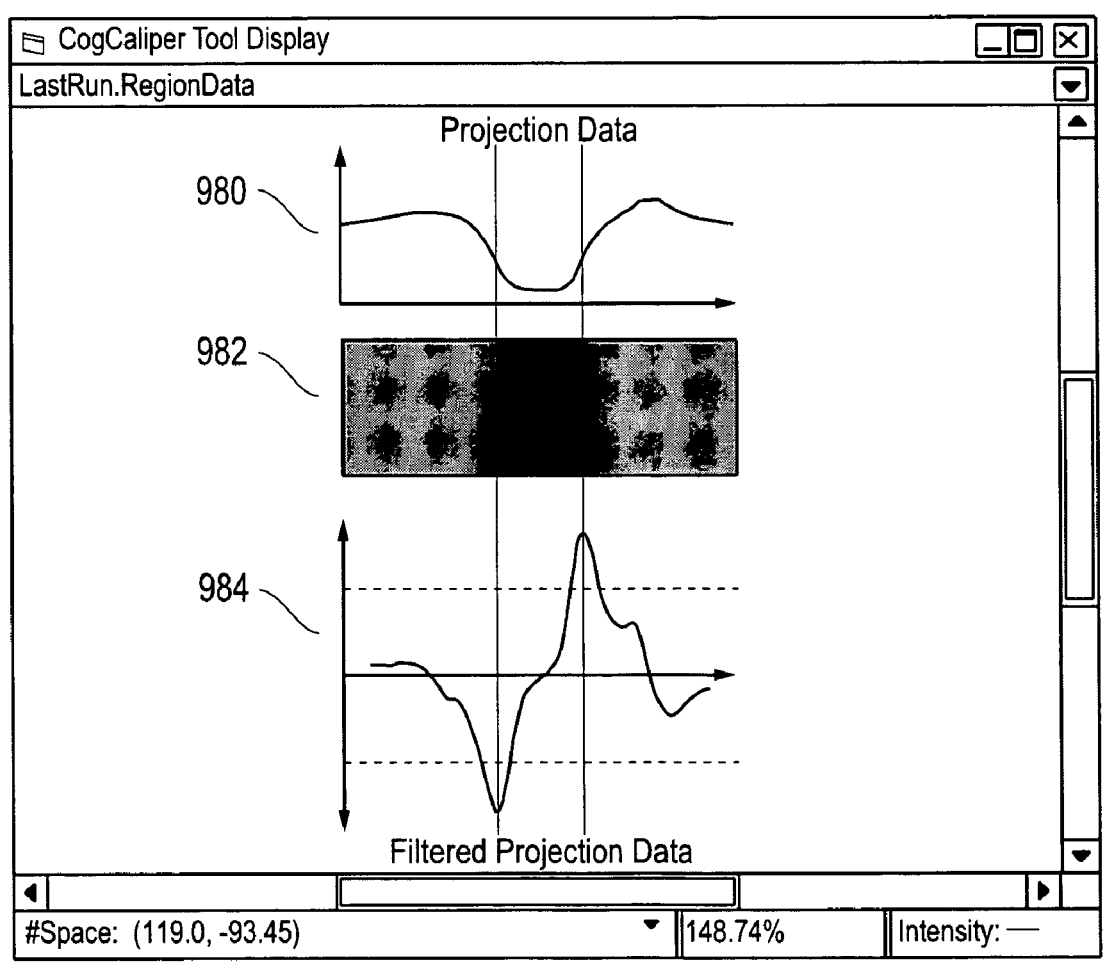
FIG. 9B graphically illustrates how an SEM image can be used in edge determination.

From the SEM image shown in FIG. 9A, the right edge 964 and left edge 962 of the line 960 are identified. The center axis 941 of fiducial 940 is also located. FIG. 9B illustrates the way an SEM image is used in edge determination. SEM image 982 is a portion of the SEM image of the fiducial. Waveform 980 is a graphical display of the grayscale average for each column of pixels in SEM image 982. Filter projection 984 is a graph of the derivative function of the grayscale averages in Waveform 980, which illustrates the fiducial edges as a maximum or minimum depending on whether the gray scale is transitioning from light to dark or dark to light. The contrast at the edges of the fiducial are thus used to assign an edge position and the mid-point between those edges is then determined.

From the SEM image, the dimensions of the cross-section can likewise be determined through the use of a similar algorithm that determines the location of two edges of the structure of interest. For example, to determine the width of a feature, the algorithm is used to assign an edge position based upon the contrast at the edges of the structure and to determine the distance between those edges. In a similar fashion, the roughness of both right and left edges can be determined by measuring and tabulating the distance between each edge and the previously determined midpoint of the fiducial. As shown in FIG. 9A, for this example the width of line 960 is calculated to be 0.164 µm, the distance between the left edge of line 960 and the fiducial center axis 941 is 0.429 µm, and the distance between the right edge of line 960 and the fiducial center axis 941 is 0.265 µm. Skilled persons will recognize that an even more accurate characterization of the width and roughness of the line could be obtained by calculating the measurements at multiple heights along the walls of the line.

After the cross-section shown in FIG. 9A has been imaged, a new cross-section along line 2 is exposed by FIB milling and imaged. The process described above is repeated for each cross section cs2 to cs8. The data from all desired cross-sections can be tabulated and stored, for example, in computer memory.

Data (in µm) for cross-sections cs1 to cs8 is shown in Table 1 below. For each cross-section cs1 through cs8, Table 1 below shows the CD measurement (in this case the width of the line) and the distance from each feature edge (right and left) to the fiducial axis. This type of data can be used to generate any of a number of known roughness parameters in order to characterize the feature surface. For example Table 1 also shows the average and 3 Sigma (the standard deviation times 3) values for the CD measurement and the distances between right and left edges and the reference. Nominal roughness values for the right and left sidewalls of each cross-section are calculated by subtracting the distance from each sidewall to reference from the average of all the cross-sections. The average and 3 Sigma values are also calculated for the nominal roughness values.

TABLE 1

| Site | CD | Right Edge to Reference | Left Edge to Reference | Nominal Roughness Right | Nominal Roughness Left |
|---|---|---|---|---|---|
| cs1 | 0.1638 | 0.2654 | 0.4292 | 0.0032 | 0.0025 |
| cs2 | 0.1634 | 0.2690 | 0.4324 | −0.0004 | −0.0007 |
| cs3 | 0.1634 | 0.2687 | 0.4320 | −0.0001 | −0.0003 |
| cs4 | 0.1635 | 0.2690 | 0.4326 | −0.0005 | −0.0009 |
| cs5 | 0.1641 | 0.2677 | 0.4318 | 0.0009 | −0.0001 |
| cs6 | 0.1633 | 0.2680 | 0.4313 | 0.0006 | 0.0004 |
| cs7 | 0.1616 | 0.2707 | 0.4323 | −0.0022 | −0.0006 |
| cs8 | 0.1618 | 0.2701 | 0.4319 | −0.0015 | −0.0003 |
| Avg. | 0.1631 | 0.2686 | 0.4317 | 0.0000 | 0.0000 |
| 3 sigma | 0.0025 | 0.0046 | 0.0030 | 0.0046 | 0.0030 |

Figure 10:
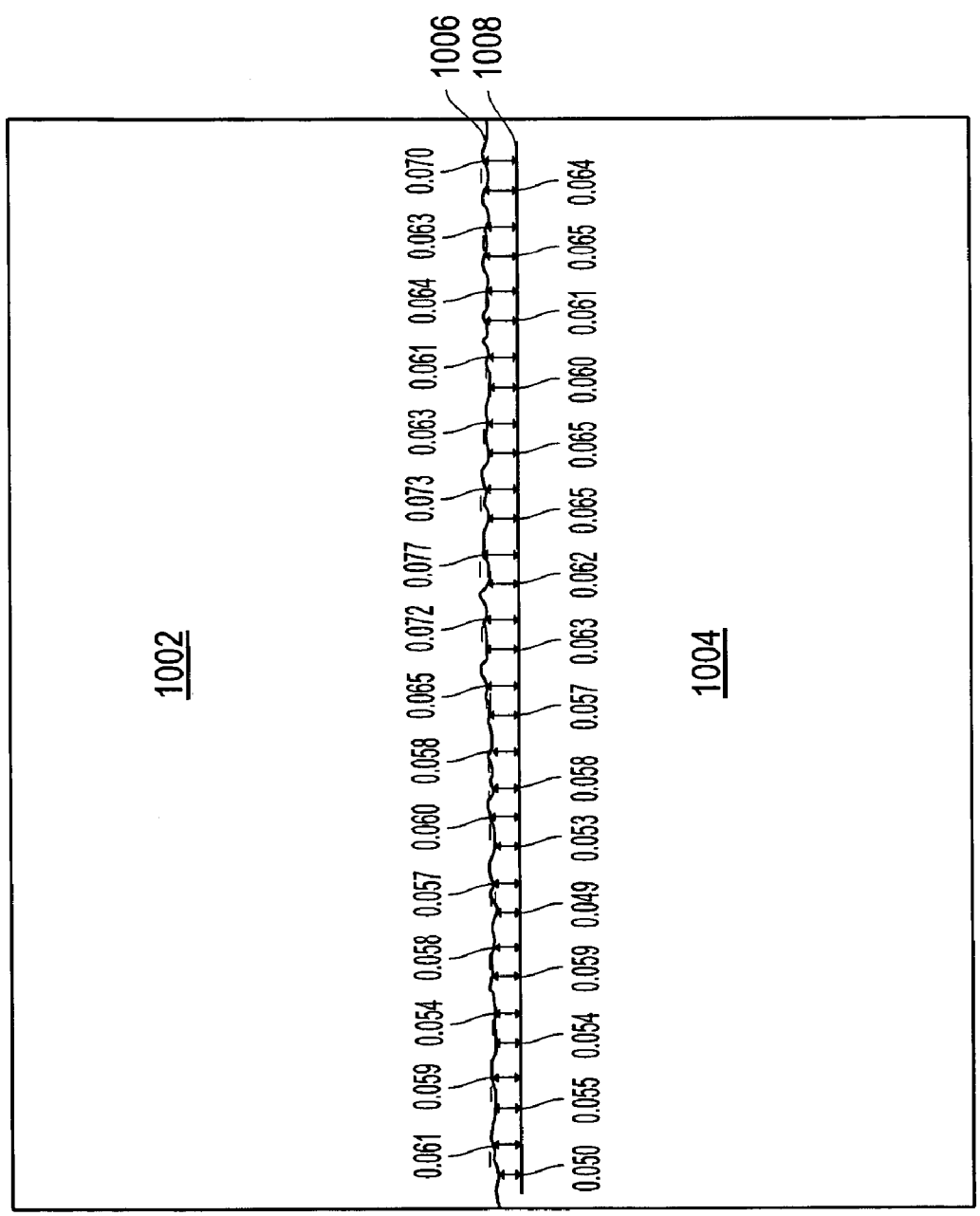
FIG. 10 shows a number of data points across a cross section of a trench floor.
Figure 1A:
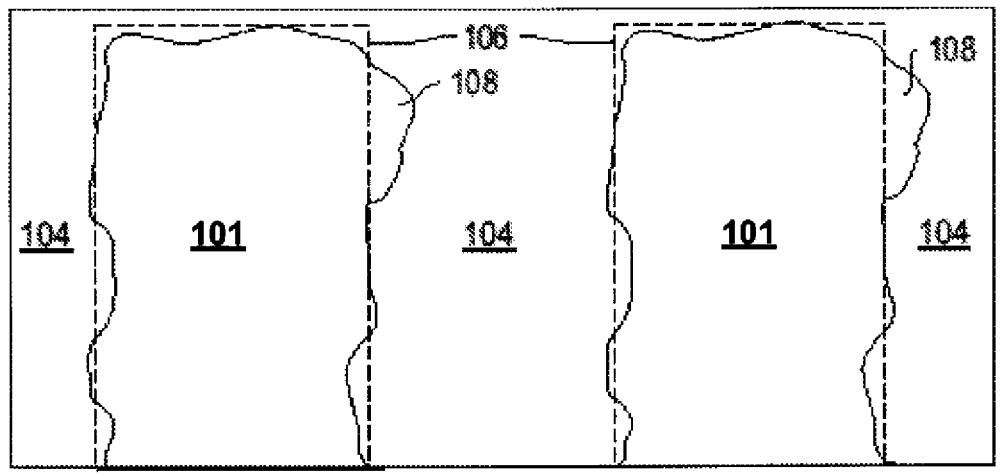
Figure 1B:
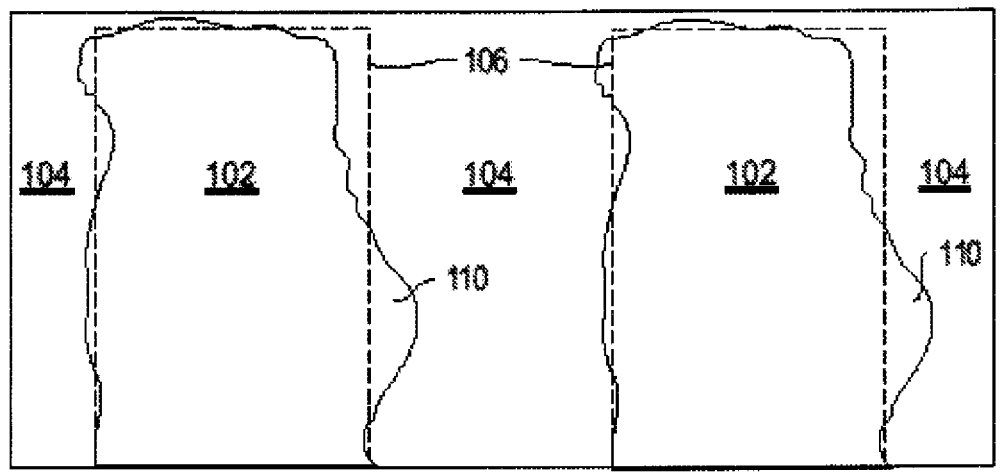
Figure 1C:
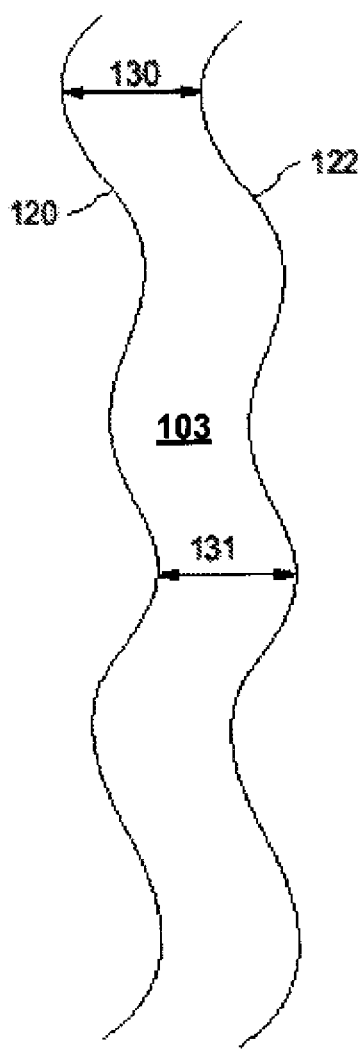
Figure 1D:
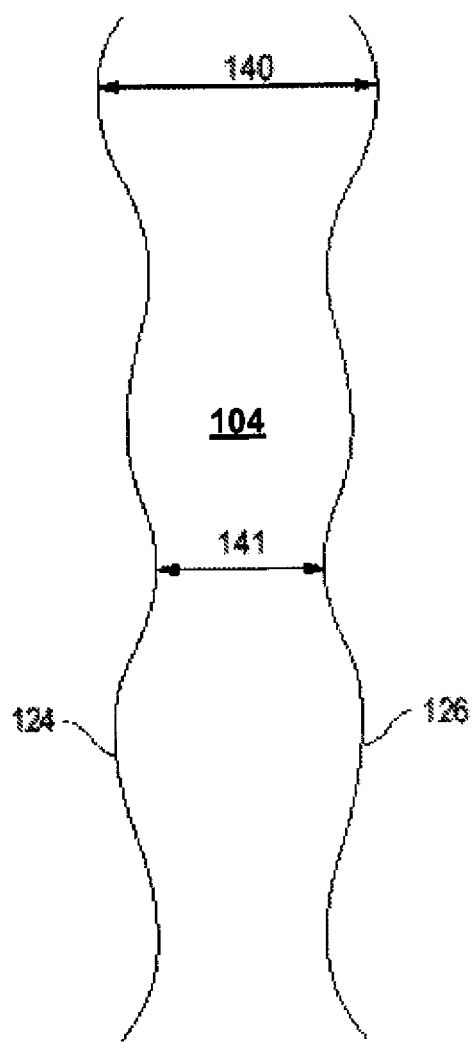

FIG. 10 shows a cross section of a trench floor, which is measured at 32 data points. This degree of detail could be desirable, for example, during process development or in process monitoring where the type of defect shown in FIGS. 7A and 7B is expected. In this SEM image, the actual surface to be measured, in this case a trench floor, is the interface 1006 between the lighter material 1002 and the darker feature material 1004. Line 1008 represents the y-axis of a fiducial (similar to the x-axis of a fiducial as shown in FIG. 9A). For each data point shown by the arrows, there is a box containing a measurement (in microns) between the interface 1006 at that point and the y-axis 1008 of the fiducial (not shown). The distances (in this case the difference in height) between the fiducial axis and the material interface at each of these data points can be used to calculate roughness across one cross-section. This data can also be combined with data from multiple cross-sections to better characterize the 3D roughness of the feature.

Although the present invention and its advantages have been described in detail, it should be understood that various changes, substitutions and alterations can be made to the embodiments described herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim:

1. A method of determining three-dimensional roughness of the surface of a feature, the method comprising:
    (a) defining the target area encompassing at least a portion of said feature surface;
    (b) imaging the target area;
    (c) locating a unique fiducial within the target area but separated from the feature, said fiducial having at least one fiducial axis substantially parallel to the feature surface;
    (d) determining the number and location of a plurality of feature cross-sections;
    (e) directing an ion beam at a the location of a first cross-section within the target area;
    (f) milling the feature in order to expose the cross-section of the feature thereby producing a substantially planar face on said exposed cross-section;
    (g) directing an electron beam at both the planar cross section and the fiducial;
    (h) determining the location of said fiducial axis;
    (i) determining the edge position for the desired feature surface on the exposed cross-section with respect to said fiducial axis;
    (j) re-imaging the target area;
    (k) re-locating the unique fiducial;
    (l) directing an ion beam at the next cross-section location within the target area;
    (m) repeating steps (f) through (l) until all cross-sections have been exposed and imaged; and
    (n) calculating an edge roughness value based upon the edge position for the desired feature surface with respect to the fiducial axis for all cross-sections.

2. The method of claim 1 in which imaging the target area comprises a partial scan of the target area with an ion beam.

3. The method of claim 1 in which defining the target area encompassing at least a portion of a feature surface further comprises depositing a protective layer of a material over the feature surface within the target area.

4. The method of claim 1 in which locating a unique fiducial within the target area but separated from the feature comprises milling a desired unique fiducial feature within the target area but separated from the feature.

5. The method of claim 1 in which determining the number and location of a plurality of feature cross-sections comprises determining the location of a first cross-section and specifying the distance between successive cross-sections.

6. The method of claim 5 in which the distance between successive cross-sections is less than 20 nm.

7. The method of claim 5 in which determining the number and location of a plurality of feature cross-sections further comprises determining the length of the feature over which said cross-sections will be located.

8. The method of claim 7 in which the length of the feature over which said cross-sections will be located comprises 1 µm to 2 µm.

9. The method of claim 1 in which milling the feature in order to expose a cross-section of the feature comprises exposing a cross-section which is substantially perpendicular to the feature surface for which three-dimensional roughness is to be determined.

10. The method of claim 1 in which milling the feature in order to expose a cross-section of the feature comprises defining a mill box having a width which is parallel to the desired cross-section and scanning an ion beam within the mill box until material has been removed to a desired depth.

11. The method of claim 10 in which the mill box width is greater than the width of the feature.

12. The method of claim 10 in which the desired depth is greater than the depth of the feature.

13. The method of claim 12 in which the width of the mill box is 1.5 times the milling depth.

14. The method of claim 1 in which determining the location of said fiducial axis comprises determining the edge positions for at least two substantially parallel fiducial surfaces and defining a line halfway between the two fiducial surfaces.

15. The method of claim 1 in which the unique fiducial has at least two fiducial axes, each substantially parallel to a feature surface to be measured.

16. The method of claim 1 in which determining the edge position for the desired feature surface comprises determining the edge position for two desired feature surfaces each parallel to the fiducial axis.

17. The method of claim 16 further comprising calculating, based upon the edge positions for the two desired feature surfaces, the maximum distance between the two feature surfaces, the minimum distance between the two feature surfaces, the volume between the two feature surfaces within the target area, or the taper angle of one of the feature surfaces.

18. The method of claim 1 in which calculating an edge roughness value comprises calculating root-mean-square roughness, peak-to-valley height, peak-to-peak roughness, spatial frequencies, or roughness orientation.

19. The method of claim 1 in which calculating an edge roughness value comprises calculating a standard deviation expressed as the square root of an average of the distances between each edge position and the fiducial axis.

20. A method for measuring the roughness of at least a portion of a surface of a feature on a workpiece, the method comprising:
   locating the feature on the workpiece;
   imaging the workpiece using a first charged particle beam column having a first field of view which includes the surface to be measured;
   selecting an identifiable fiducial within the field of view;
   directing a first charged particle beam at a first location on the feature at a known offset from the fiducial;
   milling the feature in order to expose a planar first cross-section of the surface to be measured, said first cross-section being substantially perpendicular to the surface to be measured;
   directing a second charged particle beam at the first location on the feature, said second charged particle beam having a second field of view that includes the fiducial and at least a portion of the first cross-section;
   determining the distance between the fiducial and the edge position of the surface to be measured at one or more data points on the first cross-section;
   imaging the first field of view with the first charged particle beam;
   directing the first charged particle beam at a second location on the feature at a known offset from the fiducial;
   milling the feature in order to expose a planar second cross-section of the surface to be measured, said second cross-section being substantially perpendicular to the surface to be measured;
   directing the second charged particle beam at the second location on the feature, said second charged particle beam having a second field of view that includes the fiducial and at least a portion of the second cross-section;
   determining the distance between the fiducial and the edge position of the surface to be measured at one or more data points on the second cross-section; and
   generating a three-dimensional characterization of the surface to be measured based upon the relative locations of the data points with respect to the fiducial.

21. The method of claim 20 in which generating a three-dimensional characterization of the surface to be measured comprises calculating an edge roughness value based upon the edge position for the surface to be measured.

22. The method of claim 21 in which calculating an edge roughness value comprises calculating root-mean-square roughness, peak-to-valley height, peak-to-peak roughness, spatial frequencies, or roughness orientation.

23. The method of claim 21 in which calculating an edge roughness value comprises calculating a standard deviation expressed as the square root of an average of the distances between each edge position and the fiducial.

24. A system for measuring the surface roughness of a feature, the system comprising:
   an ion beam for exposing at least two cross-sections of the feature;
   an electron beam for imaging the cross-sections and determining the distance between at least one edge of the feature and a fiducial; and
   a processing device adapted to determine the location and number of cross-sections required based upon operator input, direct the ion beam to the specified locations in order to mill the cross-sections, determine at least one edge position for the feature on each cross-section, measure the distance between each edge position and the fiducial for each cross-section, and calculate an edge roughness value for the feature surface based upon said distance and the location of each cross-section.

* * * * *

UNITED STATES PATENT AND TRADEMARK OFFICE
CERTIFICATE OF CORRECTION

PATENT NO. : 7,348,556 B2
APPLICATION NO. : 11/252115
DATED : March 25, 2008
INVENTOR(S) : Prasanna Chitturi et al.

It is certified that error appears in the above-identified patent and that said Letters Patent is hereby corrected as shown below:

In the Drawings, Sheets consisting of Figures 1A-1D should be deleted and replaced with Replacement Sheets consisting of Figures 1A-1D as shown on the attached pages.

Column 3, Line 12 – change "accelerated collimated" to read "accelerated, collimated";

Column 4, Line 64 – change "material 105" to read "material 104";

Column 5, Line 2 – change "lines 102 and 103" to read "lines 101 and 102";

Column 9, Line 39 – add "In step 321," before "Once the slicing..." to read "In step 321, once the slicing...".

Signed and Sealed this
Twenty-sixth Day of February, 2013

Teresa Stanek Rea
*Acting Director of the United States Patent and Trademark Office*